United States Patent [19]

Watson

[11] Patent Number: 4,730,931

[45] Date of Patent: Mar. 15, 1988

[54] METHOD AND APPARATUS FOR OPTICALLY MONITORING FIBER ORIENTATION IN NONWOVEN WEBS

[75] Inventor: Robert L. Watson, Kingsport, Tenn.

[73] Assignee: Eastman Kodak Company, Rochester, N.Y.

[21] Appl. No.: 866,436

[22] Filed: May 23, 1986

[51] Int. Cl.[4] .................... G01N 21/86; G01N 21/89
[52] U.S. Cl. .................................... 356/429; 250/571
[58] Field of Search ............. 356/446, 237, 429, 430, 356/431, 238, 239; 250/571, 572; 162/198, 263

[56] References Cited

U.S. PATENT DOCUMENTS

| | | | |
|---|---|---|---|
| 4,124,300 | 11/1978 | Mead et al. | 250/571 X |
| 4,414,476 | 11/1983 | Maddox et al. | 356/430 X |
| 4,490,618 | 12/1984 | Cielo | 356/429 X |
| 4,648,712 | 3/1987 | Brenholdt | 356/432 X |

Primary Examiner—Vincent P. McGraw
Attorney, Agent, or Firm—John F. Stevens; William P. Heath, Jr.

[57] ABSTRACT

Optical method and apparatus for measuring angular orientation and uniformity of orientation of fibers within a nonwoven web.

10 Claims, 9 Drawing Figures

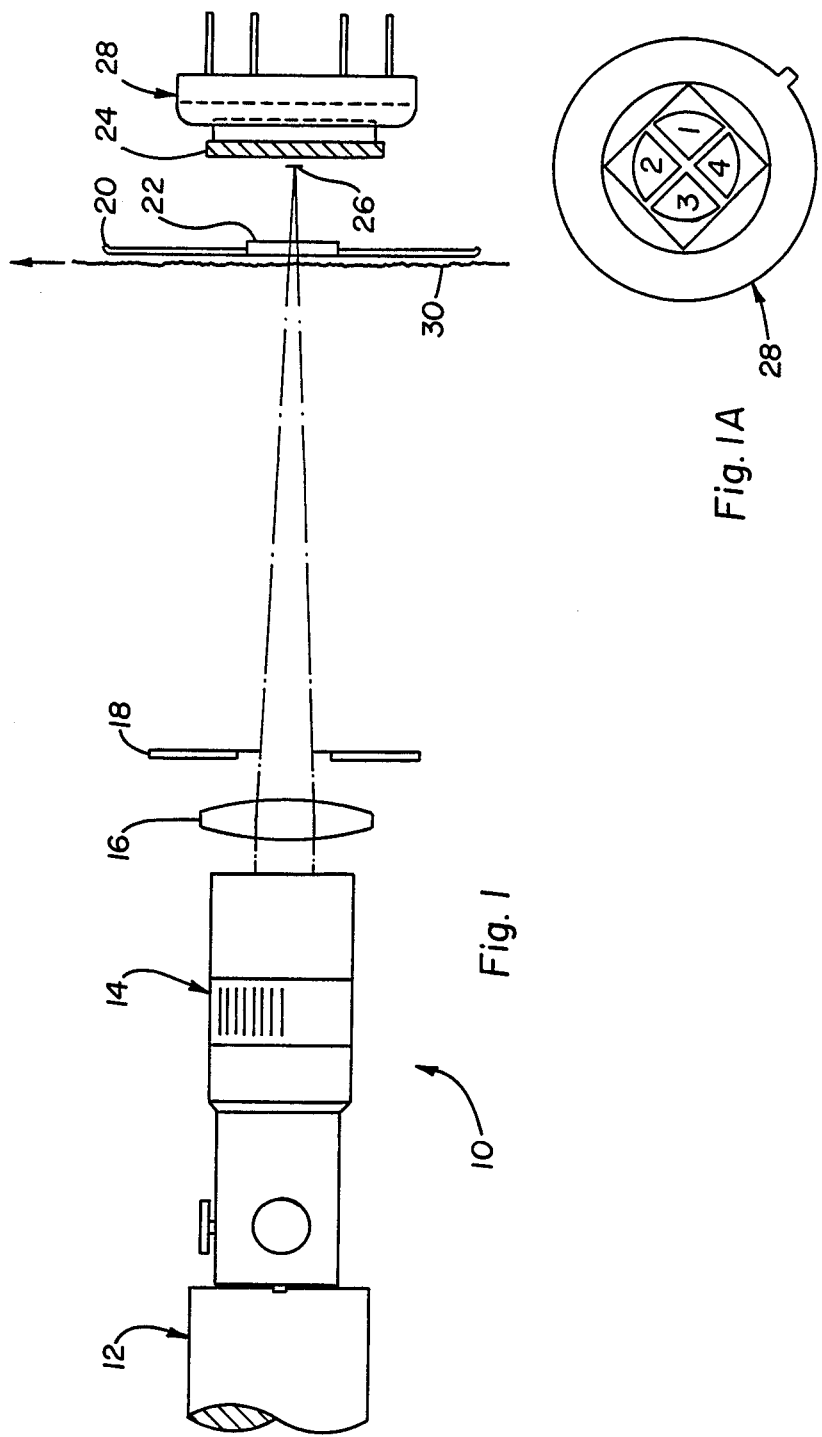

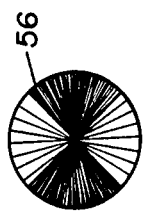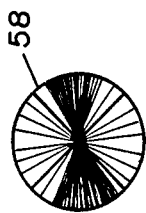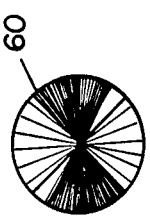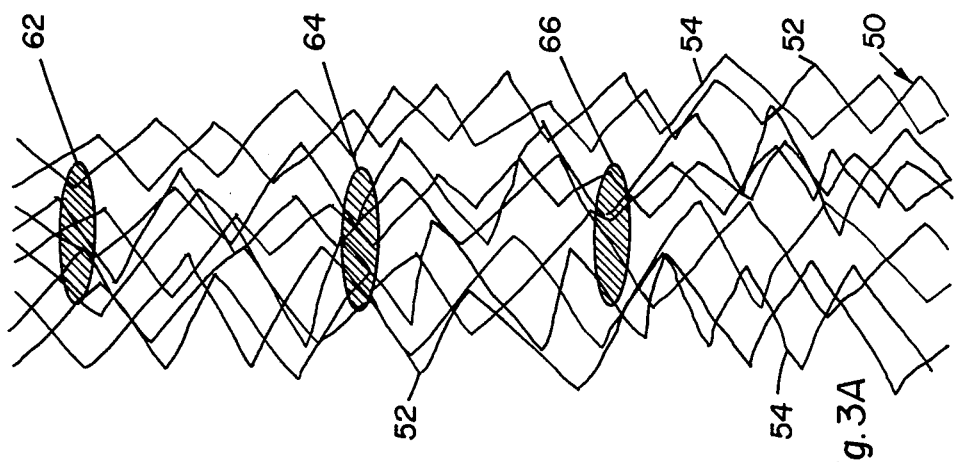
Fig. 3A
Fig. 3B
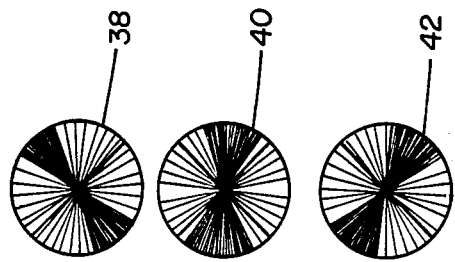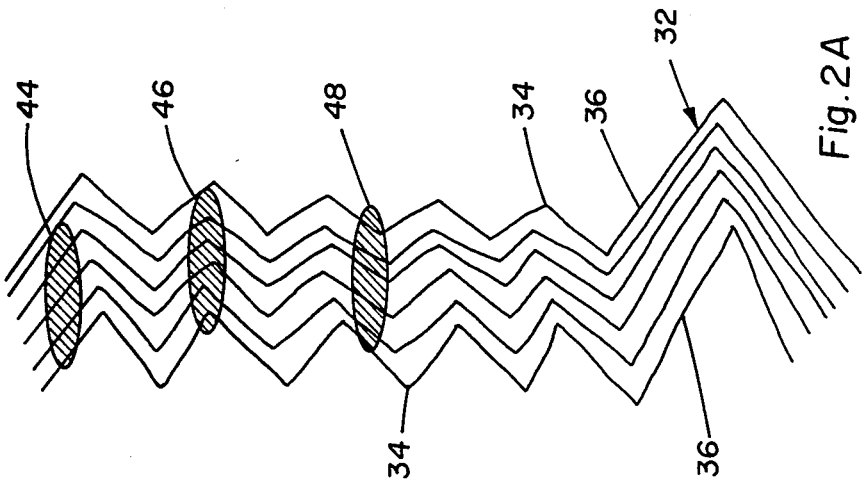
Fig. 2A
Fig. 2B

METHOD AND APPARATUS FOR OPTICALLY MONITORING FIBER ORIENTATION IN NONWOVEN WEBS

DESCRIPTION

The present invention is directed to a method and apparatus for optically measuring angular orientation and uniformity of orientation of fibers within a nonwoven web.

This invention fulfills a need for a method and apparatus alternative to the commercial practice of visual examination of webs, such as filter tow webs made from continuous filaments, for example, to determine the amount of crimp deregistration and filament separation caused by the blooming process in a plugmaker for making filter rods.

In other nonwoven webs, such as carded webs made from staple fibers, and cross-lapped structures made from staple fibers and/or continuous filaments, it is also desirable to know the ratio of Cross-machine direction machine direction orientation of fibers within the web, and the variability of that ratio. The reason for this is to see how well aligned the fibers are relative to the machine direction or how much parallelization has occurred in the machine direction. The "machine direction", is, of course, the direction in which a web is fed through a processing station.

In a plugmaker, filter tow, generally continuous filaments of cellulose acetate, undergoes a process known as "blooming" wherein mechanical means such as air jets or threaded rolls are used to cause crimp deregistration within the tow and to increase filament separation. Changes in processing conditions such as throughput speed and input tension can, if left uncompensated, cause unwanted changes in bloom. These changes can in time cause changes in weight and pressure drop in the filter element. The plugmaker makes a filter rod, which is the wrapped filter element in the form that emerges from the plugmaker. The length of the filter rod is usually four or six times the individual filter element attached to each cigarette for filtration of the tobacco smoke. A filter tip is the wrapped filter element attached to the cigarette; the tip length normally being ¼ to 1/6 the length of the filter rod.

"Pressure drop" is the resistance to air flow offered by the filter tip, and may also be referred to as "draft" or "resistance to draw".

"Blooming" is the act of separating and deregistering individual filaments in a tow or tow band from other filaments to provide the greatest amount of bulk and surface area. Tow which is "well bloomed" has essentially all of its filaments separated and deregistered.

Previously, visual observation of the filter tow by an operator as the tow runs on a plugmaker has been the only effective way available for determining the amount of blooming done by the process. The present invention has demonstrated that underbloomed, normally bloomed, and overbloomed conditions can be quantitatively distinguished. Distinguishing overbloomed and highly overbloomed conditions, however, has not yet been possible.

Underbloomed tow, for example, is comprised of filaments wherein the crimp of adjacent filaments is in good registration. Well bloomed tow, for another example, has filaments wherein the crimp of adjacent filaments is substantially deregistered.

An object of the invention, therefore, is to provide a method and apparatus to measure crimp deregistration, and thereby distinguish quantatively between underbloomed, normally bloomed, and overbloomed filter tows.

In the manufacture of some other nonwoven webs, fibers are passed through carding machines that position the fibers into relative parallel alignment in the machine direction. Then webs of parallelized fiber, as produced by successive machines and running in the same direction, may be laid on each other to form a multi-layer web. This technique produces a fabric which has high lengthwise strength but low crosswise strength. This is known as a parallel-laid web.

In a cross-laid web, after fibers are passed through a carding machine to form thin webs of parallelized fiber, the webs are crisscrossed successively on each other. This fabric has greater cross-wise strength than the parallel-laid web type.

In a random-laid web, loose fiber is blown onto a rotating, perforated drum. Internal vacuum causes the fiber to adhere to the drum, forming a heavy matte that is then passed to a lickerin, or rotating drum with teeth, which breaks up the web. These particles are blown onto a second vacuum drum forming a highly uniform web of randomly placed fibers. The thickness of the web can be regulated as required.

In these other types of nonwoven webs described above, the cross-machine direction versus the machine direction orientation ratio is also important to know as well as the variability of that ratio. In the carding machine, the speed of the scrambler roll or cross-lapper roll may be controlled by means of the present invention to obtain the desired angular orientation as measured by the orientation ratio. A faster speed will decrease the cross-machine directional strength, and a slower speed will increase crossmachine directional strength.

Another object of the invention, therefore, is to provide a method and apparatus to measure the ratio of crossmachine direction to machine direction orientation of fibers in nonwoven webs, and the variability of that ratio.

DISCLOSURE OF THE INVENTION

In accordance with the present invention, I provide a method for measuring the angular orientation and uniformity of orientation of fibers within a web and wherein the major axis of the web lies along the machine direction for feed of the web and the minor axis of the web lies perpendicular to the major axis. The method comprises selecting a cross-sectional configuration of a coherent light beam that will encompass a number of the fibers within the web sufficient to detect and record measurements of the angular orientation and uniformity; illuminating a section of the web with the coherent light beam; establishing relative movement between the web and the coherent light beam along the machine direction; and detecting refracted and diffracted components of light scattered from the fibers illuminated by the coherent light beam and determining therefrom the preferred direction of light scatter relative to the major axis and to the minor axis of the web and the variability from point-to-point within the web of such preferred direction.

In the method, the components of light scattered from fibers which are generally aligned with the major axis of the web and with the minor axis of the web are detected, and a ratio of the two detected components of scattered light and the variability of the ratio are determined.

Also in the method concerned, the coherent light beam passes through the web and the step of detecting includes detecting components of scattered light on the side of the web opposite from the source of the coherent light beam.

When the nonwoven web comprises a filter tow of crimped fibers, the step of selecting includes selecting a configuration of coherent light beam of about $\frac{1}{2}$ the wavelength of the crimp in an fiber in the web in the direction along the major axis of the web and $\geq \frac{1}{2}$ the wavelength in the direction along the minor axis of the web.

Further in the method concerned, the coherent light beam passes through the web and the step of detecting includes detecting the components of scattered light in the focal plane of the coherent light beam on the side of the web opposite from the source of the coherent light beam.

In accordance with the present invention I also provide an apparatus for measuring the angular orientation and uniformity of orientation of fibers within a web and wherein the major axis of the web lies along the machine direction for feed of the web and the minor axis of the web lies perpendicular to the major axis. The apparatus comprises an arrangement for projecting onto a section of the web a coherent light beam that will encompass a number of the fibers within the web sufficient to detect and record measurements of the angular orientation and uniformity; an arrangement for establishing relative movement between the web and the coherent light beam along the direction of the major axis; and an arrangement for detecting refracted and diffracted components of light scattered from the fibers illuminated by the coherent light beam and another arrangement for determining therefrom the preferred direction of light scatter relative to the major axis and to the minor axis of the web and the variability from point-to-point within the web of such preferred direction.

The arrangement for detecting detects components of light scattered by fibers which are generally aligned with the major axis of the web and with the minor axis of the web; and the aforementioned another arrangement for determining forms a ratio of the two detected components of scattered light and determines therefrom the variability of the ratio.

When the nonwoven web comprises a filter tow of crimped fibers, the coherent light beam has a cross-sectional configuration of about $\frac{1}{2}$ the wavelength of the crimp in an individual fiber in the web in the direction along the major axis of the web and $\geq \frac{1}{2}$ the wavelength in the direction along the minor axis of the web so as to encompass several adjacent fibers within the light beam simultaneously.

Also, in the apparatus the coherent light beam passes through the web and the arrangement for detecting is positioned on the side of the web opposite from the source of the coherent light beam.

Further, in the apparatus, the coherent light beam passes through the web and the arrangement for detecting is positioned in the focal plane of the coherent light beam on the side of the web opposite from the source of the coherent light beam.

BRIEF DESCRIPTION OF THE DRAWINGS

The details of my invention will be described in connection with the accompanying drawings, in which FIG. 1 is a diagrammatic illustration of the optical monitoring apparatus and a nonwoven web passing therethrough;

FIG. 1A is a plan view of the quadrant detector from FIG. 1 shown in enlarged form:

FIG. 2A is a diagrammatic plan view of a non-woven web of continuous filament crimped tow having well registered crimp in the plane of the nonwoven web and illustrating three different portions of the nonwoven web that are illuminated by coherent light beams;

FIG. 2B is a plan view of the focal plane at three different moments in time corresponding to the three different illuminated portions of the non-woven web shown in FIG. 2A and illustrates in the heavier shading the changing preferred directions of light scatter caused by the changing angular orientation of the fibers illuminated by the coherent light beams in FIG. 2A;

FIG. 3A is a diagrammatic plan view of a non-woven web of continuous filament crimped tow having deregistered crimp in the plane of the nonwoven web and illustrating three different portions of the nonwoven web that are illuminated by coherent light beams;

FIG. 3B is a plan view of the focal plane at three different moments in time corresponding to the three different illuminated portions of the non-woven web shown in FIG. 3A and illustrates in the heavier shading the relatively constant preferred direction of light scatter caused by the random angular orientation of the fibers illuminated by the coherent light beams in FIG. 3A;

BEST MODE FOR CARRYING OUT THE INVENTION

Figure 4:
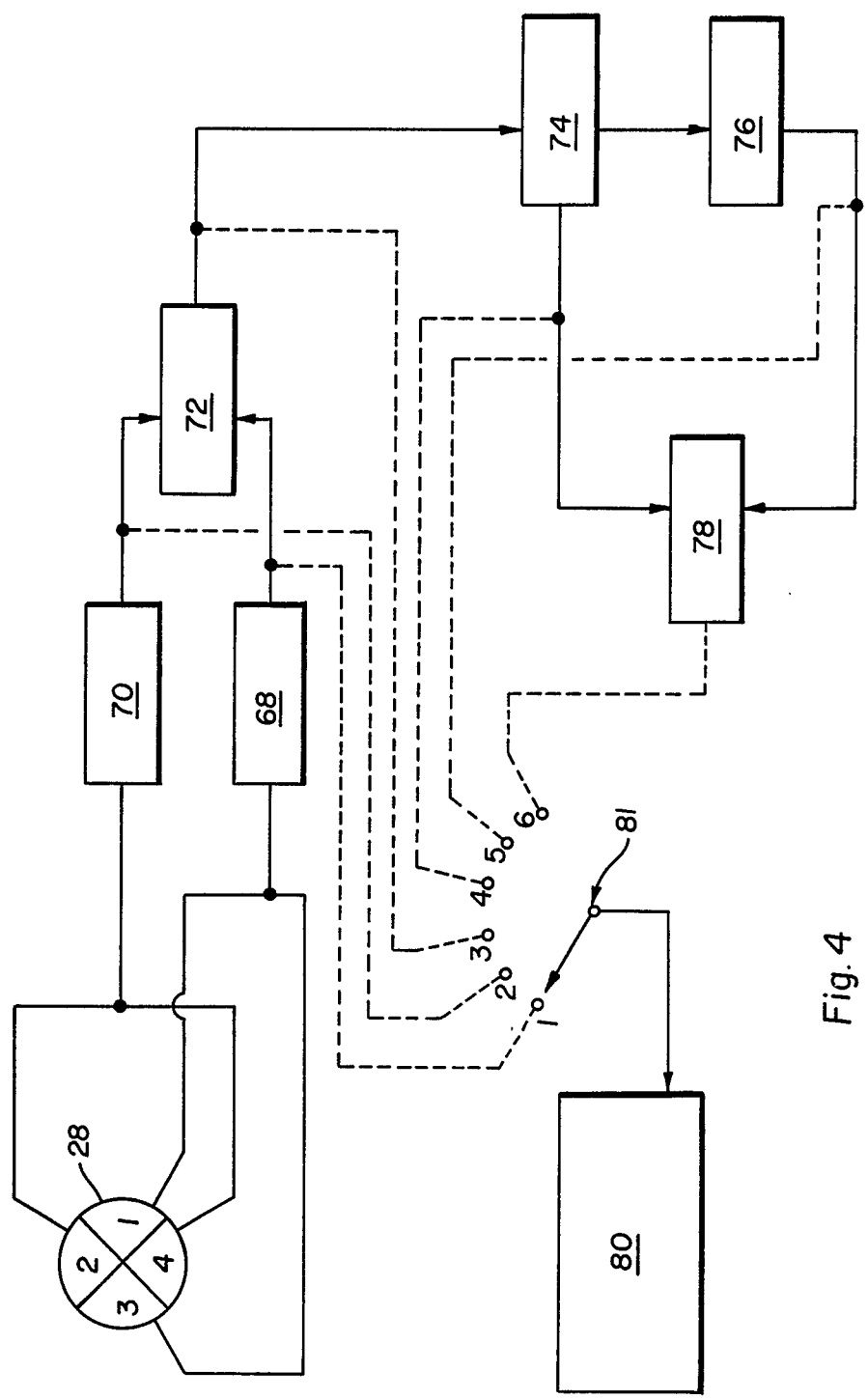
FIG. 4 is a schematic diagram of the electronic circuitry that may be associated with the optical monitoring apparatus.

In reference to FIG. 1, the optical monitoring apparatus 10 includes a low-power helium-neon laser 12, such as a Spectra-Physics Model 102R (2 MW); a beam expander and spatial filter 14, such as a Klinger SO38654 (16 power); a Fourier lens 16, such as a Klinger 911,306 (200 millimeter focal length); an iris diaphragm beam stop 18; a stainless steel reference plate 20 having an optically flat glass window 22; an interference filter 24, such as a Rolyn 66.4545, 50% T at 632.8 nanometers); an occulting dot 26 having a diameter of about 0.32 centimeter ($\frac{1}{8}$th inch); and a silicon photodiode quadrant detector 28, such as Part SD-380-23-21-251 (Active area =77 square millimeters, 9.65 millimeter diameter) from Silicon Detector Corporation.

A nonwoven web 30, which may be a filter tow of cellulose acetate continuous filaments, or a carded web of natural or man-made staple fibers, or any other type of nonwoven material of staple fibers or continuous filaments, may be intermittently or continuously advanced through the optical monitoring apparatus 10 over the stainless steel reference plate 20, which is spaced closely adjacent to the quadrant detector 28.

The low-power laser 12 provides a coherent light beam for illuminating the nonwoven web 30. Components of the coherent light beam, refracted and diffracted components of light, are caused to be scattered by the fibers or filaments as the coherent light beam passes through the nonwoven web. Light components scatter perpendicular from the fibers or filaments causing the scatter, and it is these components that are detected by the silicon photodiode quadrant detector 28 in a manner to be described.

The coherent light beam is spatially filtered by the beam expander and spatial filter 14 and expanded to a diameter of about 8 millimeters. This coherent light beam is converged by the 200 millimeter focal length convex lens 16 and its diameter is adjusted by the iris diaphragm 18. The nonwoven web 30 passes through the converging beam and it may be at a location approximately 25 millimeters upstream of the focal plane where the maximum beam diameter has been set to be 1 millimeter. (The effective beam diameter was actually somewhat less than 1 millimeter because of the Gaussian intensity profile of the laser beam). The cross-sectional configuration of the coherent light beam is selected so that it will encompass a number of the fibers within the web sufficient to detect and record measurements of the angular orientation and uniformity. When the nonwoven web comprises a filter tow of crimped fibers, for example, the configuration of the coherent light beam shall be about $\frac{1}{2}$ the wavelength of the crimp in an individual fiber in the web in the direction along the major axis (machine direction) of the web and $\geq \frac{1}{2}$ the wavelength in the direction along the minor axis (cross-machine direction) of the web.

The silicon photodiode quadrant detector 28 is positioned to lie in the focal plane mentioned above. In this position, the quadrant detector is mounted so as to collect the main cross-machine direction and machine direction components of light scattered by the fibers or filaments in the nonwoven web after the light has passed through the nonwoven side of the nonwoven web from the source of the light beam.

The coherent light beam illuminates the nonwoven web as the beam passes through the nonwoven web and the optically flat glass window 22. An occulting dot 26 on the optical axis blocks the transmitted (unscattered) light component, and the interference filter 24 for the laser wavelength blocks extraneous ambient light. The aforementioned optically flat glass window 22 is integrated into the stainless steel reference plate 20 so as to position the nonwoven web the proper distance above the quadrant detector 28.

The laser 12 and optics for shaping the coherent light beam may be mounted on a precision laboratory jack so as to enable adjustment of the coherent light beam position relative to the nonwoven web 30 along an axis transverse to the direction of nonwoven web movement, which is the cross machine direction.

The silicon photodiode quadrant detector 28 may be mounted on a five-axis lens positioner which enables the plane of the quadrant detector to be gimbaled to position it perpendicular to the coherent light beam. This arrangement also makes it possible to make X/Y/Z adjustments so that the center of the quadrant detector can be positioned at the focal point of the coherent light beam.

In reference to FIG. 1A, it will be noted that the silicon photodiode quadrant detector has photodiode segments 1 and 3 which are detecting light scattered from fibers lying generally in the machine direction and photodiode segments 2 and 4 which are detecting light scattered from fibers lying generally in the cross-machine direction relative to the advancement of the nonwoven web through the optical monitoring apparatus 10. The quadrant detector is suitably connected electronically in a manner to be described so as to form a ratio of the detected components of light scatter in the cross-machine direction to the detected components of light scatter in the machine direction. This ratio may be calculated by analog electronic circuitry and may be converted to digital form for display as will be described later.

Since light is scattered perpendicularly from the fibers or filaments in the nonwoven web, the scatter may be viewed visually to obtain an idea whether there tends to be a preferred direction to such scatter. For example, the development of this invention was based upon the premise that with respect to filter tow (nonwoven web of continuous crimped filaments), underbloomed tow is composed of filaments the crimp of which is in good registration with that of adjacent filaments. Therefore, when the tow is illuminated by a coherent light beam with the diameter of the light beam being on the order of $\frac{1}{2}$ the crimp wavelength, adjacent portions of the crimp segments will scatter light in essentially the same directions. If the coherent light beam is moved relative to the machine direction of the web, these preferred directions of light scatter change. Conversely, well-bloomed filter tow having filaments wherein the crimp in the adjacent filaments is deregistered, but having several filaments lying within the coherent light beam at any given time, would exhibit little change in the preferred direction of light scatter as the coherent light beam is scanned along the tow.

FIG. 2A, for example, diagrammatically illustrates a nonwoven web 32 in which the crimps 34 in the adjacent filaments 36 are well-registered. FIG. 2B, for example, shows the focal plane at three different moments in time 38, 40 and 42 corresponding to the diagrammatically illustrated coherent light beams 44, 46 and 48 in FIG. 2A, and illustrating the preferred directions of light scatter. The heavier shadings at 38, 40 and 42 represent such preferred directions of light scatter and illustrate how they change.

FIG. 3A, for another example, diagrammatically illustrates a nonwoven web 50 in which the crimps 52 in adjacent filaments 54 are deregistered. FIG. 3B, for example, shows the focal plane at three different moments in time 56, 58, and 60 corresponding to the diagrammatically illustrated coherent light beam 62, 64, and 66 in FIG. 3A, the preferred directions of light scatter are somewhat broader and exhibit lower variability in their angular orientation.

The components of light scatter can be grouped into those components generally parallel to the cross-machine direction or the minor axis of the nonwoven web, and those components generally parallel to the machine direction or the major axis of the nonwoven web. Using these two principal groups of components, the above-mentioned electronic circuitry will therefore determine not only a measure of the preferred direction but also the variability from point to point within the nonwoven web of such preferred direction so as to obtain a measure of registration of the crimp, when working with crimped filter tow, or the cross machine direction/machine direction fiber orientation ratio and its variability in any other type of nonwoven web.

The analog electronic circuitry will be described as follows with reference to FIG. 4: Current signals from quadrant detector photodiode segments 1 and 3 are summed up by operational amplifier 68, such as a National Semiconductor LF 356, to yield the machine direction intensity signal $I_{MD}$. Current signals from quadrant detector photodiode segments 2 and 4 are summed up by operational amplifier (National Semiconductor LF 356) 70 to yield the cross-machine direction intensity signal $I_{CMD}$. These signals, $I_{MD}$ and $I_{CMD}$, are then routed to an analog divider 72, such as a Burr-Brown DIV100JP analog divider, where they are combined to form the $I_{CMD}/I_{MD}$ signal.

The DC and AC components of the ratio signal. $I_{CMD}/I_{MD}$, are separated by an active filter section 74 using therein three operational amplifiers (not shown) such as National Semiconductor LF 356. The resulting AC component of the $I_{CMD}/I_{MD}$ signal serves as input to a converter module 76, such as a Burr-Brown 4340 RMS-to-DC converter module, which provides a measure of the standard deviation of the signal. In other words, the converter module 76 effectively squares the AC signal, integrates the squared value, and takes the square root to arrive at the RMS (root mean square) value, which is also equivalent to the standard deviation. This is divided in the analog divider 78 (Burr-Brown DIV100JP analog divider) by the DC component from the active filter section 74, which DC component is the long-term average of the intensity ratio $I_{CMD}/I_{MD}$ to calculate the % coefficient of variation (% CV) parameter. The $I_{CMD}/I_{MD}$ ratio, therefore, is a measure of preferred direction. The variability of this ratio, expressed as the % CV, is a measure of the variability of the preferred direction.

The $I_{CMD}$, $I_{MD}$, ratio of $I_{CMD}$ and $I_{MD}$, standard deviation, and % CV parameters may be displayed in digital form by means of a Teledyne 4701 (0–10V, 0–10 khz) voltage-to-frequency converter and a Newport 6130A digital counter 80. A front-panel selector switch 81 may provide a choice of any of the parameters mentioned to display.

Figure 5:
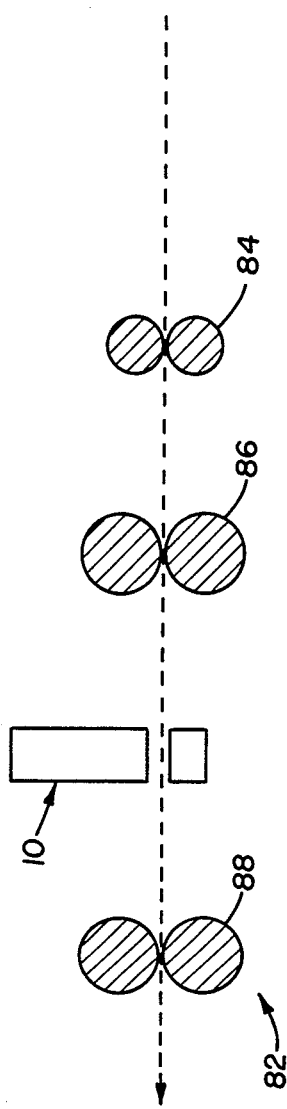
FIG. 5 is a diagrammatic illustration in elevation of a miniature tow blooming apparatus.

The following illustration represents just one of many applications that may be made of the present invention. FIG. 5 discloses a miniature tow blooming apparatus 82 on which the optical monitoring apparatus 10 of the present invention may be mounted. The miniature tow blooming apparatus, which operates in a manner well-known in the art, comprises a pair of non-driven pretension rolls 84, a pair of driven grooved rolls 86, and a pair of driven smooth rolls 88. The pair of pretension rolls 84 may be adjusted toward and away from each other so as to apply different pressures against a filter tow passing therebetween and to apply a uniform tension across the width of the filter tow. The pair of grooved rolls 86 in cooperation with the pair of pretension rolls stretches or deregisters crimped fibers in the filter tow as the filter tow passes therebetween. Finally, the pair of smooth rolls may be speeded up or slowed down relative to the speed of the driven pair of the grooved rolls 86.

Figure 6:
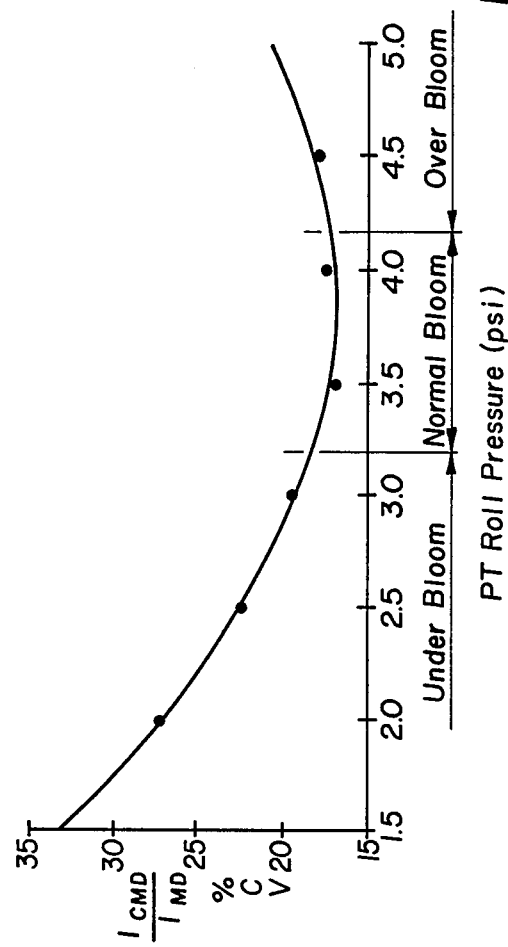
FIG. 6 is a graph illustrating a relationship between pretension roll pressure in the miniature tow blooming apparatus shown in FIG. 5 and the % CV (coefficient of variation) obtained from the optical monitoring apparatus.

Looking therefore at FIG. 6, the graph illustrated there shows the effect of application to a filter tow of different pretension roll pressures employed in the miniature tow blooming apparatus 82 of FIG. 5 as measured by the % coefficients of variation (% CV) obtained from the optical monitoring apparatus 10. The graph illustrates the areas where the filter tow proved by visual inspection to be underbloomed, normally bloomed and overbloomed. As it may be readily observed from the graph with respect to the curve illustrated, the least variability or lowest % coefficient of variation (% CV) determined by the optical monitoring apparatus occurs in the area of the curve where the tow is normally bloomed. This illustration therefore shows the effect of changing operating conditions on the nonwoven filter tow and provides a demonstration to show that there is a qualitative agreement between the operator's impression of tow blooming conditions and instrument response from the optical monitoring apparatus.

The invention has been described in detail with particular reference to preferred embodiments thereof, but it will be understood that variations and modifications can be effected within the spirit and scope of the invention.

I claim:

1. Method for measuring the angular orientation and uniformity of orientation of fibers within a nonwoven web and wherein the major axis of said web lies along the machine direction for feed of the web and the minor axis of said web lies perpendicular to said major axis, said method comprising:
   selecting a cross-sectional configuration of a coherent light beam that will encompass a number of said fibers within the web sufficient to detect and record measurements of said angular orientation and uniformity.
   illuminating a section of said web with said coherent light beam,
   establishing relative movement between the web and the coherent light beam along said machine direction, and
   detecting refracted and diffracted components of light scattered from the fibers illuminated by said coherent light beam and determining therefrom the preferred direction of light scatter relative to said major axis and to said minor axis of said web and the variability from point-to-point within said web of such preferred direction.

2. Method as defined in claim 1 wherein said components of light scattered from fibers which are generally aligned with said major axis of said web and with said minor axis of said web are detected, and a ratio of the two detected said components of scattered light and the variability of said ratio are determined.

3. Method as defined in claim 1 wherein said coherent light beam passes through said web and the step of detecting includes detecting said components of scattered light on the side of the web opposite from the source of said coherent light beam.

4. Method as defined in claim 1 wherein said web comprises a filter tow of crimped fibers and said step of selecting includes selecting a configuration of coherent light beam of about ½ the wavelength of the crimp in an individual fiber in said web in the direction along said major axis and $\geq \frac{1}{2}$ said wavelength in the direction along said minor axis of said web.

5. Method as defined in claim 1 wherein said coherent light beam passes through said web and said step of detecting includes detecting said components of scattered light in the focal plane of said coherent light beam on the side of the web opposite from the source of said coherent light beam.

6. Apparatus for measuring the angular orientation and uniformity of orientation of fibers within a nonwoven web and wherein the major axis of said web lies along the machine direction for feed of the web and the minor axis of said web lies perpendicular to said major axis, said apparatus comprising:

means for projecting onto a section of said web a coherent light beam that will encompass a number of said fibers within the web sufficient to detect and record measurements of said angular orientation and uniformity.

means for establishing relative movement between said web and said coherent light beam along the direction of said major axis, and means for detecting refracted and diffracted components of light scattered from the fibers illuminated by said coherent light beam and means for determining therefrom the preferred direction of light scatter relative to said major axis and to said minor axis of said web and the variability from point-to-point within said web of such preferred direction.

7. Apparatus as defined in claim 6 wherein said means for detecting detects components of light scattered from fibers which are generally aligned with said major axis of said web and with said minor axis of said web, and said means for determining forms a ratio of the two detected components of scattered light and determines therefrom the variability of said ratio.

8. Apparatus as defined in claim 6 wherein said web comprises a filter tow of crimped fibers and said coherent light beam has a cross-sectional configuration of about $\frac{1}{2}$ the wavelength of the crimp in an individual fiber in said web in the direction along said major axis and $\geq \frac{1}{2}$ said wavelength in the direction along said minor axis of said web so as to encompass several adjacent fibers within said light beam simultaneously.

9. Apparatus as defined in claim 6 wherein said coherent light beam passes through said web and said means for detecting is positioned on the side of the web opposite from the source of said coherent light beam.

10. Apparatus as defined in claim 6 wherein said coherent light beam passes through said web and said means for detecting is positioned in the focal plane of said coherent light beam on the side of the web opposite from the source of said coherent light beam.

* * * * *